United States Patent [19]

Simons et al.

[11] 4,139,607

[45] Feb. 13, 1979

[54] AEROSOL PROPELLANT FOR PERSONAL PRODUCTS

[75] Inventors: Charles W. Simons, Bedford; Gerald J. O'Neill, Arlington; Joel A. Gribens, Framington, all of Mass.

[73] Assignee: W. R. Grace & Co., Cambridge, Mass.

[21] Appl. No.: 822,353

[22] Filed: Aug. 5, 1977

Related U.S. Application Data

[63] Continuation-in-part of Ser. No. 714,522, Aug. 16, 1976, Pat. No. 4,041,148, which is a continuation-in-part of Ser. No. 622,246, Oct. 14, 1975, abandoned.

[51] Int. Cl.$^2$ .................. C09K 3/30; A61K 7/00; A61K 9/00
[52] U.S. Cl. .................. 424/45; 252/305; 424/47
[58] Field of Search .................. 424/45, 47; 252/305

[56] References Cited

U.S. PATENT DOCUMENTS

| 3,502,588 | 3/1970 | Winberg | 252/188.3 |
|---|---|---|---|
| 3,887,439 | 6/1975 | Hutchinson | 203/63 |
| 3,922,228 | 11/1975 | Hutchinson | 252/67 |
| 3,996,153 | 12/1976 | Heeb | 424/45 |
| 4,041,148 | 8/1977 | Simons | 424/45 |

*Primary Examiner*—Anna P. Fagelson
*Attorney, Agent, or Firm*—Lowell H. McCarter; C. Edward Parker

[57] ABSTRACT

Certain fluorinated dimethyl ethers have been found to possess the stability, the compatibility and sufficient freedom from deleterious physiological effects to be used as aerosol propellants in cosmetic, hygienic, pharmaceutical and other personal products. Bis(difluoromethyl) ether is also free of the chlorine atoms believed responsible for some destruction of ozone in the upper atmosphere. Bis(difluoromethyl) ether and carbon dioxide provides a combined gaseous and liquefied propellant system having improved aerosol pattern and emptying characteristics and eliminates the compressed gas effect usually shown by use of carbon dioxide in propellant systems.

8 Claims, No Drawings

AEROSOL PROPELLANT FOR PERSONAL PRODUCTS

CROSS-REFERENCE TO RELATED APPLICATION

This application is a continuation-in-part of application Ser. No. 714,522 filed on Aug. 16, 1976, now U.S. Pat. No. 4,041,148 which in turn is a continuation-in-part of application Ser. No. 622,246 filed on Oct. 14, 1975, now abandoned.

THE PRIOR ART

The task of finding acceptable replacements for the widely used halocarbon aerosol propellants is not an easy one. Over the years, most compounds capable of generating the necessary pressures under packing conditions have been tried, and the industry has settled for reasons of performance, safety and cost on a relatively limited number of gaseous liquefiable hydrocarbons, chlorofluorocarbons and a few other common non-toxic gases such as nitrous oxide and carbon dioxide.

Until recently, chlorofluorocarbons such as propellant 11 (trichloromonofluoromethane) and propellant 114 (dichlorotetrafluoroethane), to name a few, appeared ideally suited for aerosol propulsion in terms of stability, chemical inertness, compatibility with aerosol package ingredients, lack of toxicity and pressure-generating capacity. While they still benefit from this excellent combination of physical and chemical properties within the aerosol pack area, their continued use is being increasingly challenged because of their alleged deleterious effect on the layer of ozone in the upper atmosphere of the planet. In these circumstances, the search for acceptable substitutes has become imperative. Propellant systems must be located that possess essentially the same assortment of properties as the chlorofluorocarbons but are free of the ozone-destroying chlorine.

In this respect, a review of the art for chlorine-free, stable compounds capable of generating the necessary pressures did not prove very fruitful. For instance, a few patents exists which teach the use of dimethylether as aerosol propellant (U.S. Pat. No. 1,800,156). The extreme flammability of this compound, however, accounts for its lack of favor over the years even though attempts have been made to circumvent part of its disadvantages by spraying it together with an aqueous aerosol phase (U.S. Pat. No. 3,207,386). As to the possibility of altering this undesirable facet of what might otherwise be an acceptable propellant, by fluorination for instance, the art would only lead the skilled practitioner to negative conclusions about said possibilities. In terms of chemical stability, to begin with, it is known that halogenation of the alpha-carbon of methyl ethers causes instability in the molecule. Thus, compounds such as $CHF_2.O.CH_3$ decompose either on standing or on distillation, $CH_2F.O.CHF_2$ decomposes in glass, while other fluorinated methyl ethers are unstable under hydrolytic conditions such as may be found in aerosol preparations. The fluorinated methyl ethers did not therefore appear very promising on that account.

More importantly from the point of view of ecology, safety and health with which the present invention is concerned, it must be realized that whatever limited knowledge was available on the physiological properties of fluorinated ethers was certainly not conducive to the selection of such compounds for use as propellants in aerosol packaging, especially of personal products such as toiletries and medicinals. Note the words of Larsen in this respect [Fluorine Chemistry Rev., Vol. 3 (1969), page 20] when he states that "as a class, fluorinated ethers show the widest spectrum of unpredictable biological response, with some being extremely potent convulsants while others are excellent anesthetics." Obviously, neither of these properties has any appeal for uses such as those presently contemplated. A striking illustration of what can be expected from fluorinated ethers in general is afforded by the fact that bis(2,2,2-trifluoroethyl) ether, a compound very closely related chemically to that of the present invention, can evoke seizures in rats at concentrations as low as 30 parts per million (weight/volume). It is interesting to note also that this particular diethyl ether finds use as a therapeutic convulsant in mental therapy [Goodman & Gilman, The Pharmacological Basis of Therapeutics, 4th edition, pages 355–6, The MacMillan Co. (1970)]. There is no need to list here any later published data in support in Larsen's views on fluorinated alkyl ethers. Let us just say that the recent developments in the fields of anesthesia and mental therapy generally confirm these views.

As to the aerosol field, the most recent pertinent art reveals that two new azeotropic mixtures composed of pentafluorodimethyl ether and dimethyl ether can be used, inter alia, as propellants (U.S. Pat. No. 3,922,228). The impact of this specific disclosure on the newly discovered utility of the two ethers with which the present application is concerned shall be discussed later in conjunction with the disclosure of the biological behavior of the components of said azeotropic mixtures. More recently the patent art (see U.S. Pat. No. 3,996,153) teaches that gaseous carbon dioxide can be dissolved in certain solvents to provide a propellant system. However, from data in the patent, such a solvent-gaseous carbon dioxide system appears to leave a significant quantity of the pack in the aerosol container when the gas pressure has fallen to about 75% of the starting pressure. This then is the field in which the present inventors prospected in order to find the substitutes for the chlorofluorocarbon propellants that are eagerly sought by industry and government agencies such as EPA (Chem. Eng. News, Concentrates, Jan. 12, 1976).

SUMMARY OF THE INVENTION

It has now been discovered that a superior aerosol propellant system is a combination of liquefied bis(difluoromethyl) ether and gaseous carbon dioxide wherein the gaseous propellant is from about 0.5 to about 4.0 weight percent based on weight of the bis(difluoromethyl) ether. These compounds do not contain any chlorine and will not therefore contribute to the destruction of atomspheric ozone that is said to take place when conventional chloride-containing propellant gases accumulate in the upper atomsphere. Furthermore, the bis(difluoromethyl) ether has been found to be stable and non-toxic, unlike other known fluorinated methyl ethers.

DETAILED DESCRIPTION

The ether compound used in the present invention is a symmetrical dimethyl ether on which at least two of the hydrogen atoms on each carbon have been replaced by fluorine atoms. Bis(difluoromethyl) ether has been found to possess the correct combination of physical, chemical and biological properties which allows its use in aerosol packaging. It is stable on storage, resistant to alkaline hydrolysis and is not flammable, even in direct contact with a torch. The boiling point for bis(difluoromethyl) ether is −2° C. which corresponds to a vapor pressure of 20 psig under standard conditions of temperature and pressure.

Perfluorodimethyl ether has a boiling point of −55° C. and a vapor pressure, under standard conditions of temperature and pressure, of 210 psig. Therefore there is no need to use a gaseous propellant with the perfluorodimethyl ether described and claimed in parent application, now U.S. Pat. No. 4,041,148.

The combination of the liquefied propellant, bis(difluoromethyl) ether and the gaseous propellant, carbon dioxide, yields unexpectedly superior aerosol patterns and results in the complete discharge of the contents from the aerosol package as the data in the examples herein will demonstrate. Other known propellants, i.e., trichlorofluoromethane (Freon 11), methylene chloride when combined with gaseous carbon dioxide do not provide satisfactory aerosol patterns nor is there a complete discharge of the contents of the aerosol package.

In preparing an aerosol package, the desired pressure is achieved by mixing bis(difluoromethyl) ether and carbon dioxide with other liquids involved in the aerosol preparation and this in whatever proportions indicated by the conditions at hand. The propellant system of this invention may also be used together with other conventional gaseous aerosol propellants in order to achieve various purposes such as changes in compatibility with specific aerosol preparation ingredients, cost, rate of delivery and the like. Among usable propellants of that class are conventional gases such as nitrous oxide, non-halogenated hydrocarbons as well as fluorohydrocarbons, preferably — in view of the principal object of the present invention, those that do not contain any chlorine atoms. As to the liquid carrier for the product to be dispensed, which does affect the ultimate vapor pressure of the pack, it is selected from conventional materials including ethyl alcohol in a weight ratio up to 50:50 with bis(difluoromethyl) ether, perchloroethylene, trichloroethylene, acetone, amyl acetate, water and the like. Dimethyl ether up to about 50% by weight may be included in the propellant system without detracting from the benefit of using the bis(difluoromethyl) ether-carbon dioxide combination.

In addition to the properties already described for the ether-carbon dioxide propellant system of this invention, it must be noted that at the concentrations likely to be created when aerosol products with which they are packed are dispensed, no deleterious physiological effects will take place. The compounds are not toxic and do not cause convulsions. Only a mild anesthetic activity results when mice are exposed to bis(difluoromethyl) ether for a two hour period. The active species, the tetrafluoro compound, compares favorably in fact with plain dimethyl ether in that it has a greater safety margin than the latter, as indicated by the standard anesthetic index (A.I.) value for each compound, said values being >3 and 1.3, respectively.

In view of the known chemical instability of ethers in which hydrogen atoms on the alpha-carbon have been replaced by fluorine atoms — an instability which yields toxic products such as hydrogen fluoride for example, and also in view of the number of known fluorinated dialkyl ethers which cause convulsions when administered to mammals in small concentration, the ethers of this invention were tested for biological activity. The conventional tests that were carried out yielded the following data:

BIOLOGICAL TESTING OF FLUORINATED DIMETHYL ETHERS

Bis(difluoromethyl) ether. Mice were exposed to various concentrations vapors of the ether in a chamber equipped with a bed of soda lime to absorb carbon dioxide. The procedure used is standard for evaluation of inhalation anesthetic and is similar to that of Robbins [Pharmacology and Experimental Therapeutics 86, 197 (1946)]. Ten mice were exposed to each concentration tested for a period of two hours. It was thus determined that bis(difluoromethyl) ether is anesthetic but not toxic at concentrations of up to slightly more than 20% by volume and that the recovery time of mice anesthetized with the material is about 2 minutes. No deaths were observed during and after exposure at those levels. The anesthetic index of the tetrafluoromethyl ether was determined to be >3 which compares favorably, from the safety point of view, with that of dimethyl ether, 1.3. The safety of the fluorinated ether was further determined by exposing rats to a 5% concentration during 3 hours a day for 5 days, with no signs of convulsions nor deaths being noted.

Perfluorodimethyl ether. This compound was tested by exposing 6 mice a concentration of vapors as high as 75% by volume for a period of 60 minutes. No recognizable biological effect was noted during and after exposure. This is quite different from the behavior of the hexafluorodiethyl ether discussed in the prior section which causes convulsions in rats at 30 ppm.

Pentafluorodimethyl ether. This compound was tested, again by exposing six mice to various vapor concentrations for a period of 60 minutes. All mice died either within 75 minutes of exposure or by the next morning when concentrations of 50, 25 and 12.5% were used. No discernable effects were noted at 6 and 9% vapor concentrations. Upon autopsy, it appeared that the mice died of pulomonary edema. Stable concentrations of the ether during the test and the results of gas chromatography monitoring of the vapors substantially ruled out the presence of both initial impurities and later breakdown or metabolic products of the ether.

The picture that emerges from these tests and from the fluorinated alkyl ether prior art discussed earlier is that two ethers one of which is used in this invention are surprisingly different from most such alkyl ethers, and especially from the pentafluorodimethyl ether that has been said to have some utility, not by itself, but as a member of an azeotropic mixture with dimethyl ether (U.S. Pat. No. 3,922,228).

However, as the data shows, that pentafluoro compound is not suited for use in aerosolized personal products, such as toiletries and medicines, which must come in intimate contact with the user in order to be effective.

The following examples are provided to illustrate various non-limiting embodiments of the invention. Unless otherwise noted, all proportions used are on a weight basis. Also in each preparation the propellant, the ethyl alcohol and the aerosol can are cooled to −25° C. to facilitate the loading operation.

EXAMPLE 1

Aerosol containers were loaded with carbon dioxide and (1) octafluorocyclobutane, (2) bis(difluoromethyl) ether, (3) trichlorofluoromethane (CFCl$_3$, Freon 11), (4) methylene chloride and (5) 1,2dichloro,1,1,2,2 tetrafluoroethane ($C_2Cl_2F_4$ Freon 114) respectively. The propellants were combined with approximately an equal weight of denatured ethanol and the aerosol dispersion and spray patterns examined. Ethanol was used as the pack material in order to evaluate the aerosol patterns produced by various liquefied-carbon dioxide combinations.

| Liquid Propellant | Wt. of Liquid Propellant,gms | Wt. of $CO_2$,gms | Wt. of Ethanol,gms | Aerosol Pattern |
|---|---|---|---|---|
| $C_4F_8$ | 39.9 | 0.9 | 39.9 | Good |
| $(CF_2H)_2O$ | 32.3 | 1.0 | 31.7 | Good |
| $CFCl_3$ | 35 | 0.8 | 35.7 | Poor |
| $CH_2Cl_2$ | 31.3 | 0.9 | 31.9 | Poor |
| $CF_2ClCF_2Cl$ | 25.8 | 0.6 | 25.8 | Fair |

From this it is seen that commonly used liquefied propellants $CFCl_3$, $CF_2ClCF_2Cl$ and $CH_2Cl_2$ when combined with gaseous carbon dioxide does not provide acceptable aerosol patterns. Lesser known liquefied propellant octafluorocyclobutane when combined with carbon dioxide does provide an acceptable spray pattern showing the unpredictable behavior of liquefied propellants when combined with carbon dioxide.

EXAMPLE 2

An aerosol container was loaded with 25 grams of ethanol and pressurized with gaseous carbon dioxide to a pressure of 50 psig. The spraying characteristics were extremely poor. The discharge of the ethanol was essentially a pressure discharge with very little break up of the ethanol stream. An acceptable aerosol spraying pattern was not obtained.

EXAMPLE 3

Bis(difluoromethyl) ether, 23.1 g, was added to denatured ethanol, 26.7 g. The resulting mixture has a vapor pressure of 5 psig. Despite this low pressure value, an aerosol system activited by this mixture formed a good aerosol spray. By adding a small quantity of gaseous carbon dioxide, i.e., less than 0.5 g. to the bis(difluoromethyl) ether liquefied propellant a low pressure formulation having an enhanced aerosol pattern and complete pack discharge characteristics may be manufactured.

This particular type of low pressure formulation is singularly suitable for pressurizing glass-contained aerosol systems such as are preferred for esthetic reasons for dispensing perfumes, colognes and other toiletries.

EXAMPLE 4

A mixture consisting of 50.43% dimethyl ether and 49.57% bis(difluoromethyl) ether was found to have a vapor pressure of 40 psig. When this mixture 46 g was placed in an aerosol can with denatured ethanol, 45 g, giving a 1:1 mix, a fine aerosol spray could be produced.

Mixtures of this type are particularly suitable as propellants for inhaled aerosols. These are metered and of small capacity, so that the flammability and abuse potential of dimethyl ether are limited. The technique, on the other hand, renders available on the virtues of dimethyl ether, namely its benign action on the heart, a vapor pressure sufficiently high (62 psi at room temperatures) to permit blending with bis(difluoromethyl) ether, and, because of solvent capacity, a probably high compatibility with drugs.

By substituting gaseous carbon dioxide for a portion or all of the dimethyl ether in this example all concern for the flammability and abuse potential are essentially eliminated.

EXAMPLE 5

Aerosol containers were loaded with carbon dioxide and (1) trichlorofluoromethane ($CFCl_3$, Freon 11), (2) methylene chloride, (3) bis(difluoromethyl) ether ($CHF_2OCHF_2$), and (4) octafluorocyclobutane ($C_4F_8$) along with ethanol as in Example 1 above. The initial pressure and weight of the contents in each container was noted. The contents of each container was then discharged through an aerosol valve and the remaining pressure and/or the contents remaining in each container were recorded at various stages until the container pressure was 0 or until all the contents were discharged, whichever occurred first. The results are tabulated below. The aerosol patterns for octafluorocyclobutane and bis(difluoromethyl) ether were good, while poor aerosol patterns were observed with trichlorofluoromethane and methylene chloride.

| Propellant System | Pressure in Container psig | Wt. of Contents Remaining g.m | Total Wt. Discharged gm. | % of Contents Discharged |
|---|---|---|---|---|
| $CFCl_3/CO_2$ | 41 | 55.7 | 0 | 0 |
| | 36 | 49.9 | 5.8 | 10.4 |
| with Ethanol | 30 | 42.7 | 13.0 | 23.3 |
| | 26 | 36.0 | 19.7 | 35.4 |
| | 20 | 27.7 | 28.0 | 50.3 |
| | 16 | 20.5 | 35.2 | 63.2 |
| | 10 | 9.3 | 46.4 | 83.3 |
| | 6 | 2.8 | 52.9 | 94.8 |
| | 0 | 1.3 | 54.2 | 97.3 |
| $CH_2Cl_2/CO_2$ | 41 | 50.2 | 0 | 0 |
| | 36 | 46.2 | 4.0 | 8.0 |
| with Ethanol | 30 | 40.7 | 9.5 | 18.9 |
| | 26 | 34.7 | 15.5 | 30.9 |
| | 20 | 27.6 | 22.6 | 45.0 |
| | 16 | 20.8 | 28.9 | 57.6 |
| | 10 | 11.5 | 38.2 | 76.1 |
| | 6 | 5.2 | 44.5 | 88.6 |
| | 0 | 0.9 | 48.8 | 97.2 |
| $CHF_2OCHF_2CO_2$ | 43 | 53.3 | 0 | 0 |
| | 40 | 48.9 | 4.4 | 8.3 |
| with Ethanol | 36 | 42.9 | 10.4 | 19.5 |
| | 30 | 32.1 | 21.2 | 39.8 |
| | 26 | 22.7 | 30.6 | 57.4 |
| | 20 | 13.2 | 40.1 | 75.2 |
| | 14 | 0 | 53.3 | 100.0 |

-continued

| Propellant System | Pressure in Container psig | Wt. of Contents Remaining g.m | Total Wt. Discharged gm. | % of Contents Discharged |
|---|---|---|---|---|
| $C_4F_8/CO_2$ | 54 49.4 | 0 | 0 | |
|  | 50 | 37.1 | 12.3 | 24.9 |
| with Ethanol | 44 | 12.9 | 36.5 | 73.9 |
|  | 40 | 8.3 | 41.1 | 83.2 |
|  | 35 | 4.1 | 45.3 | 91.7 |
|  | 30 | 2.3 | 47.1 | 95.3 |
|  | 25 | 0 | 49.4 | 100.0 |
| $CFCl_3/CO_2$ | 26 | 54.3 | 0 | 0 |
|  | 20 | 49.6 | 4.7 | 8.6 |
| with Ethanol | 16 | 41.8 | 12.5 | 23.0 |
|  | 12 | 32.0 | 22.3 | 41.1 |
|  | 8 | 21.3 | 33.0 | 60.8 |
|  | 4 | 16.3 | 38 | 70.0 |
|  | 0 | 6.0 | 48.3 | 89.0 |
| $CH_2Cl_2/CO_2$ | 29 | 53.2 | 0 | 0 |
|  | 22 | 43.3 | 9.9 | 18.6 |
| with Ethanol | 18 | 38.9 | 14.3 | 26.9 |
|  | 15 | 34.4 | 18.8 | 35.3 |
|  | 10 | 28.3 | 24.9 | 46.8 |
|  | 6 | 21.2 | 32.0 | 60.2 |
|  | 0 | 15.2 | 38.0 | 71.4 |
| $C_4F_8/CO_2$ | 45 | 53.8 | 0 | 0 |
| with Ethanol | 40 | 39.2 | 14.6 | 27.1 |
|  | 36 | 31.2 | 22.6 | 42.0 |
|  | 30 | 22.3 | 31.5 | 58.6 |
|  | 25 | 11.3 | 41.9 | 77.9 |
|  | 20 | 3.8 | 50.0 | 92.9 |
|  | 12 | 0 | 53.8 | 100.0 |

The data in this example teaches incomplete discharge of contents using the well known liquefied propellants Freon 11 and methylene chloride in combination with carbon dioxide. Complete discharge of contents is obtained using a propellant system comprising carbon dioxide and bis(difluoromethyl) ether. The value of this discovery from a customer acceptance standpoint is clear.

EXAMPLE 6

A 3% by weight solution of sorbitan trioleate was made in bis(difluoromethyl) ether. There appeared to be no miscibility problems. Sorbitan trioleate is commonly used as a vehicle for pharmaceutical aerosols such as, for instance isoproterenol sulfate.

By adding a very small quantity of gaseous carbon dioxide, i.e., about 0.5 to 2.0 weight percent based on total pack, a pharmaceutical aerosol allowing complete discharge of aerosol container contents is prepared.

It will be evident to the man skilled in the art that the aerosol pressurizing system disclosed here can be employed with a large number of conventionally aerosol packaged materials such as toiletries, household and personal hygienic products, pharmaceuticals and medicines, and generally any other type of product generally packed with the chlorofluoroalkanes of the art, especially when the mode of use of such product involves a toxicity potential for living species. Furthermore, it shall be found in many instances that in terms of compatibility with both organic and inorganic materials, the bis(difluoromethyl) ether-carbon dioxide propellants system of the present invention are superior to the oxygen-free molecules of the chlorofluoroalkanes.

What we claim is:

1. An aerosol container pressurized by a propellant system consisting essentially of liquefied bis(difluoromethyl) ether and gaseous carbon dioxide.

2. The container of claim 1 wherein the propellant system contains from about 0.5 to about 4.0 weight percent carbon dioxide based on weight of bis(difluoromethyl) ether.

3. The container of claim 2 wherein the propellant system additionally contains up to 50% by weight of dimethyl ether.

4. The container of claim 2 wherein the bis(difluoromethyl) ether is mixed with denatured ethanol in a weight ratio of about 50:50.

5. The container of claim 2 in which medicinals are packaged.

6. The container of claim 2 in which pharmaceuticals are packaged.

7. The container of claim 2 in which sorbitan trioleate is packaged.

8. The container of claim 4 wherein the propellant system additionally contains about 50% by weight dimethyl ether based on weight of bis(difluoromethyl) ether.

* * * * *